United States Patent
Nino et al.

(10) Patent No.: US 10,219,854 B2
(45) Date of Patent: *Mar. 5, 2019

(54) MODULAR CLUTCH ASSEMBLY

(71) Applicant: ECA Medical Instruments, Newbury Park, CA (US)

(72) Inventors: John Nino, Simi Valley, CA (US); David Ivinson, Camarillo, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 15/243,454

(22) Filed: Aug. 22, 2016

(65) Prior Publication Data

US 2016/0354132 A1    Dec. 8, 2016

Related U.S. Application Data

(63) Continuation of application No. PCT/US2015/022308, filed on Mar. 24, 2015.

(Continued)

(51) Int. Cl.
*A61B 17/88*    (2006.01)
*A61B 90/00*    (2016.01)
(Continued)

(52) U.S. Cl.
CPC .......... *A61B 17/8875* (2013.01); *A61B 90/03* (2016.02); *B25B 23/141* (2013.01); *B25B 23/1427* (2013.01); *A61B 2090/031* (2016.02)

(58) Field of Classification Search
CPC ... B25B 23/141; B25B 23/1427; A61B 90/03; A61B 2090/031; A61B 17/8875
(Continued)

(56) References Cited

U.S. PATENT DOCUMENTS 1,744,976 A * 1/1930 Levedahl .............. B25B 23/141
                                                      81/475
7,025,151 B2    4/2006 Hehli et al.
(Continued)

FOREIGN PATENT DOCUMENTS

WO    WO 2011/139902 A2    11/2011
WO    WO 2013/143563 A1    10/2013

OTHER PUBLICATIONS

International Patent Application No. PCT/US2015/022308; Int'l Search Report and the Written Opinion; dated Jun. 30, 2015; 11 pages.

(Continued)

*Primary Examiner* — David B Thomas
(74) *Attorney, Agent, or Firm* — Baker & Hostetler; Mark H. Krietzman (57) ABSTRACT

A clutch within a torque-limiting device which may include a shaft extending axially through a clutch assembly and a spring to connect to a nut. The clutch having swappable gear rings. The upper and lower shanks may be under a force from the spring and further configured to selectively engage within a predetermined torque limit and disengage at above the predetermined torque limit. Accordingly, the shaft may receive torque up to the predetermined limit as provided by a user operating a handle of the torque-limiting device. The torque-limiting device may be disposable, reusable, economical, and have high torque capabilities.

23 Claims, 5 Drawing Sheets

Related U.S. Application Data (60) Provisional application No. 61/973,657, filed on Apr. 1, 2014.

(51) Int. Cl.
   *B25B 23/14* (2006.01)
   *B25B 23/142* (2006.01)

(58) Field of Classification Search
   USPC .................................................. 81/467, 475
   See application file for complete search history.

(56) References Cited

U.S. PATENT DOCUMENTS

| | | | | |
|---|---|---|---|---|
| 7,272,998 | B1 * | 9/2007 | Gauthier | B25B 23/141 |
| | | | | 81/473 |
| 7,431,136 | B2 * | 10/2008 | Simm | B25B 21/00 |
| | | | | 192/110 B |
| 7,467,576 | B2 | 12/2008 | Gao | |
| 7,650,821 | B2 * | 1/2010 | Gauthier | B25B 23/141 |
| | | | | 81/467 |
| 9,162,350 | B2 * | 10/2015 | Nino | B25B 15/04 |
| 9,241,751 | B2 * | 1/2016 | Nino | B25B 13/466 |
| 9,242,357 | B2 * | 1/2016 | Nino | B25B 23/141 |
| 9,259,258 | B2 * | 2/2016 | Laurenti | B25B 23/1427 |
| 9,409,285 | B2 * | 8/2016 | Ivinson | A61B 17/8875 |
| 9,445,873 | B2 * | 9/2016 | Nino | A61B 17/8883 |
| 9,446,507 | B2 * | 9/2016 | Nino | A61B 17/8875 |
| 9,877,764 | B2 * | 1/2018 | Nino | A61B 17/8875 |
| 9,931,741 | B2 * | 4/2018 | Nino | B25B 23/141 |
| 2006/0179981 | A1 | 8/2006 | Cutler et al. | |
| 2012/0247241 | A1 | 10/2012 | Takahashi et al. | |
| 2012/0291599 | A1 * | 11/2012 | Cutler | B25B 15/02 |
| | | | | 81/475 |
| 2013/0226192 | A1 | 8/2013 | Nino et al. | |
| 2013/0319190 | A1 | 12/2013 | Nino et al. | |
| 2013/0327190 | A1 | 12/2013 | Laurenti | |
| 2016/0030101 | A1 * | 2/2016 | Nino | B25B 15/04 |
| | | | | 81/475 |
| 2016/0354581 | A1 * | 12/2016 | Ivinson | A61M 25/0113 |
| 2016/0354906 | A1 * | 12/2016 | Nino | A61B 17/8875 |

OTHER PUBLICATIONS

European Patent Application No. 15772178.8; Extended Search Report; dated Oct. 30, 2017; 9 pages.

* cited by examiner

FIG. 5C

MODULAR CLUTCH ASSEMBLY

CROSS-REFERENCE TO RELATED APPLICATIONS

This application is a Continuation of International Patent Application PCT/US2015/022308, filed Mar. 24, 2015, which claims priority to U.S. Provisional Patent Application Ser. No. 61/973,657, filed on Apr. 1, 2014, the content of which is incorporated herein by reference in its entirety.

FIELD

This disclosure relates to a modular clutch assembly and, in particular, to a medical use disposable torque-limiting in-line driver with a hybrid plastic-metal gear that disengages at a predetermined torque limit.

GENERAL BACKGROUND

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded. Devices imparting Torque as high as about 106 lbf-in are traditionally not disposable due to the high forces, which they must withstand.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Piecemeal drivetrain systems have been developed to gear-up or otherwise impart greater torque with disposable devices. Such piecemeal systems provide interchangeability of parts to a device, within which torque is transferred from part-to-part of a piecemeal system.

DISCLOSURE

Briefly stated, torque devices according to implementations of the present disclosure obviate the shortfalls of piecemeal systems by reducing the number of part-to-part transitions of torque.

A swappable fortified gear ring is disclosed. The gear ring has a front side with gear teeth and a backside with ½ of a latch and catch mating system. The latch on the back side fit into corresponding catches on a shank. The clutch mechanism for a torque limiting device has two gear rings=, with teeth facing each other and each supported on a shank. The latch/catch connection between shank and gear ring allows one molded set of shanks to be adaptable to accommodate a variety of gear rings fitted thereon.

of exemplary implementations disclosed herein include a fortified clutch assembly torque-limiting driver having a body, a handle; a lower cylindrical shank affixed to a first gear ring having a drive socket; an upper cylindrical shank affixed to a second gear ring; a nut; a coil spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the hardened first gear ring, and the spring and connected to the nut; and, wherein the gear ring of the upper cylindrical shank and the gear ring of the lower cylindrical shank engage for relative rotation, and wherein the gear rings disengage when a predetermined torque limit is exceeded.

Aspects of exemplary implementations disclosed herein include a fortified clutch assembly torque-limiting driver having a body, a handle; a lower cylindrical shank affixed to a first gear ring having a drive socket; an upper cylindrical shank affixed to a second gear ring; a nut; a coil spring between the upper cylindrical shank and the nut, wherein the spring is configured to apply a force across the upper cylindrical shank and the lower cylindrical shank and force provided by the spring securely maintains the drive connection of the shaft engaged within the drive socket of the lower cylindrical shank; a shaft having a workpiece-engaging tip and a drive connection engaged within the drive socket of the lower cylindrical shank, the shaft extending axially through the lower cylindrical shank, the hardened first gear ring, and the spring and connected to the nut; and, wherein the gear ring of the upper cylindrical shank and the gear ring of the lower cylindrical shank engage for relative rotation, and wherein the gear rings disengage when a predetermined torque limit is exceeded. In some instance the driver includes at least one washer between the lower cylindrical shank and the body. In some instance the driver includes a first washer between the spring and nut. . In some instance the driver includes a first washer and a second Delrin washer between the spring and nut.

Aspects of exemplary implementations disclosed herein include a fortified clutch assembly torque-limiting driver wherein each gear ring is affixed to respective shanks via latches and mating catches.

Aspects of exemplary implementations disclosed herein include a fortified clutch assembly torque-limiting driver wherein each gear ring is hardened.

Aspects of exemplary implementations disclosed herein include a fortified clutch assembly torque-limiting driver wherein each gear ring is 440c stainless steel.

Aspects of exemplary implementations disclosed herein include a fortified clutch assembly torque-limiting driver wherein each gear ring is 440c stainless steel and affixed to respective shanks via latches and mating catches.

Aspects of exemplary implementations disclosed herein include a fortified clutch assembly torque-limiting driver having a body, a handle; a lower cylindrical shank affixed to a first gear ring having a drive socket; an upper cylindrical shank affixed to a second gear ring; a nut; a coil spring between the upper cylindrical shank and the nut, wherein the spring is configured to apply a force across the upper cylindrical shank and the lower cylindrical shank and force provided by the spring securely maintains the drive connection of the shaft engaged within the drive socket of the lower cylindrical shank; a shaft having a workpiece-engaging tip and a drive connection engaged within the drive socket of the lower cylindrical shank, the shaft extending axially through the lower cylindrical shank, the hardened first gear ring, and the spring and connected to the nut; and, wherein the gear ring of the upper cylindrical shank and the gear ring of the lower cylindrical shank engage for relative rotation, and wherein the engaged gear rings and affixed shanks will provide a predetermined torque of at least 12 Newton-meters (Nm) of force over at least one of 5, 10, 20, 30, 40, 50,60, 70, 80, 90, 100, 105, 110, 120 actuations. In some instance the driver includes at least one washer between the lower cylindrical shank and the body. In some instance the driver includes a first washer between the spring and nut. In some instance the driver includes a first washer and a second Delrin washer between the spring and nut.

Aspects of exemplary implementations disclosed herein include a fortified clutch assembly torque-limiting driver having a body, a handle; a lower cylindrical shank with a first hardened gear ring affixed to a front side and having a drive socket through the nose at the opposite side; an upper cylindrical shank with a second hardened gear ring affixed to the bottom face and having a front facing side; a nut; a spring between the front facing end the upper cylindrical shank and the nut, wherein the spring is configured to apply a force across the gear rings; a shaft having a workpiece-engaging tip and a drive connection engaged within the drive socket of the lower cylindrical shank, the shaft extending axially through the lower cylindrical shank, the hardened first gear ring, the second hardened gear ring, the upper cylindrical shank and the spring and connected to the nut; and, wherein the hardened gear ring of the upper cylindrical shank and the hardened gear ring of the lower cylindrical shank engage for relative rotation, and wherein the gear rings disengage when a predetermined torque limit is exceeded. In some instances the engaged gear rings and affixed shanks will provide a predetermined torque of at least 12 Newton-meters (Nm) of force over at least one of 5, 10, 20, 30, 40, 50,60, 70, 80, 90, 100, 105, 110, 120 actuations. In some instance the driver includes at least one washer between the lower cylindrical shank and the body. In some instance the driver includes a first washer between the spring and nut. In some instance the driver includes a first washer and a second Delrin washer between the spring and nut.

Aspects of exemplary implementations disclosed herein include a fortified clutch assembly torque-limiting driver having a body, a handle; a lower cylindrical shank with a first hardened gear ring affixed to a front side and having a drive socket through the nose at the opposite side; an upper cylindrical shank with a second hardened gear ring affixed to the bottom face and having a front facing side ;a nut ;a spring between the front facing end the upper cylindrical shank and the nut, wherein the spring is configured to apply a force across the gear rings; a shaft having a workpiece-engaging tip and a drive connection engaged within the drive socket of the lower cylindrical shank, the shaft extending axially through the lower cylindrical shank, the hardened first gear ring, the second hardened gear ring, the upper cylindrical shank and the spring and connected to the nut; and, wherein the hardened gear ring of the upper cylindrical shank and the hardened gear ring of the lower cylindrical shank engage for relative rotation, and wherein the gear rings disengage when a predetermined torque limit is exceeded. In some instances the engaged gear rings and affixed shanks will provide a predetermined torque of at least 12 Newton-meters (Nm) of force over at least one of 5, 10, 20, 30, 40, 50,60, 70, 80, 90, 100, 105, 110, 120 actuations. In some instances there are a plurality of upper dog cavities (UDC) in the bottom face of the upper shank; a plurality of dog latches extending from the front side of the second hardened gear ring; and, whereby the dog latches mate with the UDC thereby affixing the gear ring to the upper shank. In some instances there are a plurality lower dog cavities (LDC) in the face of the lower shank; a plurality of dog latches extending from a front side of the first hardened gear ring; and, whereby the dog latches mate with the LDC thereby affixing the gear ring to the lower shank.

Aspects of exemplary implementations disclosed herein include a fortified clutch assembly torque-limiting driver having a body, a handle; a clutch assembly; a nut; a spring; a shaft having a workpiece-engaging tip extending axially through the clutch and the spring and connected to the nut; and, wherein the spring is configured to apply a force across the clutch; wherein the clutch disengages when a predetermined torque limit is exceeded. In some instances each gear ring in the clutch assembly is constructed of 440c stainless steel. In some instances the engaged gear rings will provide a predetermined torque of at least 12 Newton-meters (Nm) of force over at least one of 5, 10, 20, 30, 40, 50,60, 70, 80, 90, 100, 105, 110, 120 actuations.

DRAWINGS

The above-mentioned features of the present disclosure will become more apparent with reference to the following description taken in conjunction with the accompanying drawings wherein like reference numerals denote like elements and in which.

As shall be appreciated by those having ordinary skill in the art, the figures are not to scale, and modifications to scale within a figure or across the figures are considered within the present disclosure.

FURTHER DISCLOSURE

According to one or more exemplary implementations, as shown in FIGS. 1A-5C, disclosed are aspects of an inline torque-limiting device 100. Torque-limiting device 100 includes a distal end 2 and a proximal end 4 of an axially extending generally hollow cylindrical body 2 with a distal end 3 which terminates from the cylindrical body 2 toward tip 12 of shaft 14. The proximal end 4 forms a mount 1010 for drive shaft 1000 which may be connected to a powered device.

In some exemplary implementations there is disclosed a body 2 with a cylindrical end 18 herein a lower shank 200 fits into in a movable fashion. The lower shank 200 provided, is shown with an annularly tapering body and nose cone 8 along its length. Lower shank 200 may have a plurality of support flanges 10 that add strength while saving material. At one end, lower shank 200 tapers to drive shaft guide 15 at the end of the nose cone 8 molded to engage drive connection 16 of shaft 14. An exemplary implementation shows, at least in part, shaft 14 provided, at one end, with workpiece-engaging tip 12, adapted for engagement with an associated workpiece, such as a fastener or the like. Workpiece-engaging tip 12 is shown to be a hexagonal wrench, but could be a screwdriver, wrench, or any other tool arrangement. At an opposite end, lower shank 200 has a plurality of lower dog cavities (LDC) 202 arranged in a face 203 with a circumferential rim 204 extending radially outward and an internal axial bore 205 to accommodate at least a portion of shaft 14 extending there through.

A first and second hardened gear ring 300 and 350 are interposed between the lower shank and upper shank 400 via reinforced catches wherein the hardened gear rings and shank combination operate within a predetermined range of torque and duty cycles without failure. In some instances hardened refers to a stainless steel gear ring. In other instances hardened refers to plastics or other metal or alloys such as Titanium and aluminum. One hardened material suitable for the gear ring is 440c stainless steel which will withstand at least 12 Newton-meters (Nm) of force over and 100 actuations .The hardened gears are functional over a number of cycles and force that would cause failure of a plastic gear arrangement such as that taught in International Application WO 2011/139902 which is hereby incorporated by this reference as if fully set forth herein. The predetermined range is preferably between 70 lbf-in and about 150 lbf-in, more preferably between about 90 lbf-in and about 135 lbf-in, most preferably between about 106 lbf-in and about 125 lbf-in. In some instance the torque range is above 125 lbf-in. In some instance the hardened gear must withstand at least 100 actuations and remain in a specified operational range. In some instance the hardened gear must withstand at least 50 actuations and remain in a specified operational range.

According to aspects of one or more exemplary implementations, inside cylindrical body 2 a clutch assembly is disposed. The clutch assembly includes first gear ring 300 and second gear ring one fixed to each of the shanks. In use the upper shank 300 and attached second gear ring 350 forcibly engages the first gear ring 300 and attached lower shank 200.

Upper shank 400 has a bottom face 402 and a front facing side 403, the front face 402 has a plurality of upper dog cavities (UDC) 405 and the upper shank 400 includes outer cylindrical shank 407 and axial bore 409 through inner shank 411. Inner shank 411 and outer shank 407 are connected via inner supports arms 412, leaving upper shank 400 substantially hollow with internal spaces on a top face. Alternatively, upper shank 400 may be of a single contiguous piece. The upper shank also has recess 80 formed therein for engagement with a drive protrusion within the cylindrical body 6 (shown in FIG. 4).

The four UDCs 405 are reinforced catches. The four LDCs 202 are also reinforced catches. Although four UDC and LDC are illustrated, the choice of four is not a limitation. Those of ordinary sill in the art will recognize that a fewer or greater number of UDC or LDC may be implemented depending on the material, use, force and duty cycle are within the scope of this disclosure. In some instance as few as two LDC or UDC in other instances three, four, five or even six LDC or UDC may be utilized. More than six LDC or UDCs would require a bottom face of enough area to provide separate cavities. The number of LDCs and UDS need not be equal. In some instances it is preferable to align one UDC with the recess 80. It is preferably to have at least 2 recesses on opposite sides of the outer shank 407. By aligning two of the UDCs with the recess 80 the load is distributed better across the shank. In some instances 2 or more arms 412 are opposite each other and one is aligned with the recess. The arm 412 placement above UDCs also provides additional support and strength.

Figure 3:
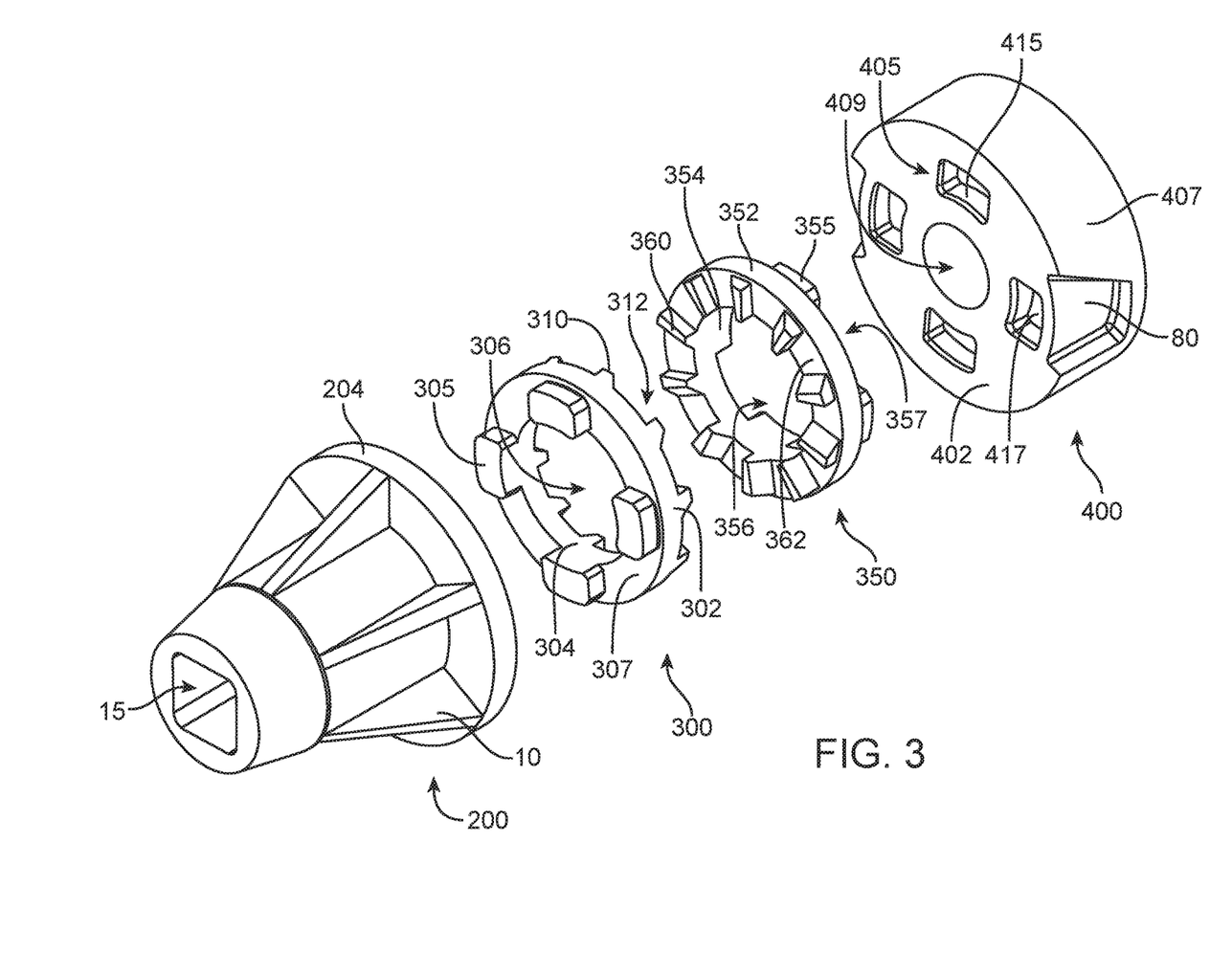
FIG. 3 shows an assembly view of the modular clutch assembly.

FIG. 3 shows UDCs 405 as closed catches with an annular wall 415 and a substantially bottom 417. The bottom 417 secures the annular wall and provides additional strength to prevent failure. The bottom may be a completely closed region or it may have an open center region (not shown). The cavity structure of the LDC 202 is substantially the same as that of the UDC 405. The depth of the UDCs corresponds to the length of the preferably between about 0.069" and about 0.090" more preferably between about 0.069" and about 0.075" and most preferably about 0.072÷.

However, the depth and opening configuration of the UDC or LDC must be corresponding to the corresponding dogs that acted as catches therein. Specifically, the first gear ring 300 has an outer annular wall 302 and in inner annular wall 304 forming a ring with an open center 306 and dog latches extending from a front side 307 and gear teeth 310 extending from the backside 312 of the ring. Specifically, the second gear ring 350 has an outer annular wall 352 and in inner annular wall 354 forming a ring with an open center 356 and dog latches 355 extending from a front side 357 and gear teeth 360 extending from the backside 362 of the ring. The length of a drive dog is preferable greater than the length of the opposing gear teeth so the lateral force generated by the gear teeth is less than the lateral force between the drive dog and the UDCs.

The length of each latch corresponds to the depth of each catch (UDC or LDC) however, it is small enough to fit into the cavity (catch). For purposes of a 0.072" catch depth for a UDC or LDC a suitable length for a dog latch would be about 0.062". The delta between depth and length is in part a factor of the UDC or LDC having a radiuses edge at its bottom connection with its annular wall and the dog latch should not extend so far as to damage the radiuses boundary. If the boundary radius was reduced the dog latch length could increase accordingly. For additional fortification, the length of dog latches are preferably longer than they are wide.

The width of the dog latches is relative to the anticipated force and the material. Since a steel dog will be interfacing with a softer material in the catch UDC or LDC, a dog latches' width should correspond to the anticipated force. The width and the thickness of the dogs create the surface area that applies the force to the catches. A greater width (more total surface area) applies less stress to the catch.

The gear ring should also sit flat against the face of the shank it is fit to. FIG. 2C shows the upper shank 400 with a bottom face 402 against which the front side 357 of the second gear ring will rest once the dog latches 355 are mated with the corresponding UDCs 405. The gear ring should seat completely against the mating surface of the bottom face 402 of the clutch prior to the gear ring drive dogs reaching the bottom of the cavities.

The thickness of the drive dog should be thicker than the thickness of the gear teeth 310/360 plus the gap between the opposing gear teeth when the device is static. This ratio of dog latch length to gear teeth presents a loose gear ring from becoming dislodged. Once assembled, there is typically about a 0.005" gap between the gear rings. The gap ensures the top of the teeth do not touch the base of the opposing gear ring. If the two features touch and drag against each other during actuations, that would affect the torque output and stability.

Those of ordinary skill in the art will recognize that in some instance that at least one of the hardened gear rings may be sonically bonded to a plastic shank, and that such sonic bonding is within the scope of this disclosure although it is less robust and its use will be dependent on the forces involved and the duty cycle required and such variation is within the scope of this disclosure. In some instances of less than the highest levels of torque sonic bonding may be added to add strength and allow for smaller UDC or LDC.

Those of ordinary skill in the art will recognize that in some instance that at least one of the hardened gear rings may, in addition to being fit into a face of a shank with dog latches in catches, may also be sonically bonded to the plastic shank and such variation is within the scope of this disclosure.

Figure 4:
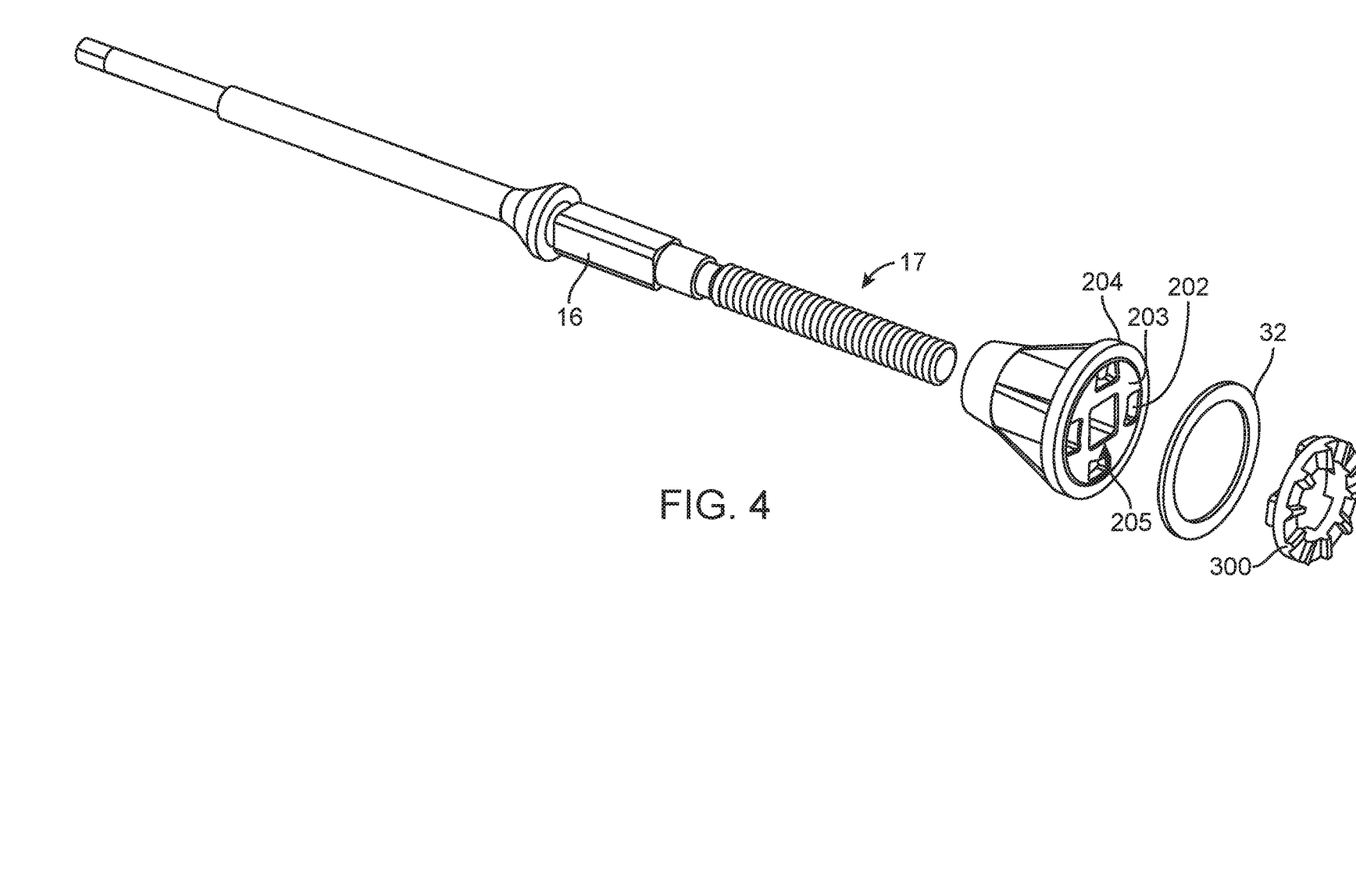
FIG. 4 shows a partial assembly view of some aspects of the clutch assembly.

According to one or more exemplary implementations, upper shank 400 includes at least one recess 80 on a side of outer shank 407. Recess 80 is provided as a cylindrical cut, relief or recess into the side of the outer shank and maybe provided as a square or rectangular cut or the cut may have a slanted side or sides relative to the axis of upper shank 400, as shown in FIG. 3. According to aspects of one or more exemplary implementations, integrally formed within cylindrical body 2, protrusion 85 mates with recess 80 of upper shank 400. FIG. 3 and FIG. 4 illustrate protrusion 85 in relation with recess 80. Protrusion 85 extends inward in a radial fashion and has a length along the axis of cylindrical body 2 for relative moveable engagement within recess 80. This engagement provides a locking mechanism of shaft 14 relative to the handle via upper shank 400 when pressure is applied across lower shank 200 and upper shank 400. Recess 80 is provided circumferentially wider than protrusion 85 for allowing cylindrical body 6 and the handle to rotate in reverse a predetermined distance from a locked positio2 without subsequent reverse rotation of workpiece-engaging tip 12. Thus, at least one recess 80 and at least one protrusion 85 lock the handle in one direction providing the necessary torque to drive a fastener and allow for a predetermined amount of reverse rotation before unscrewing the fastener.

In assembly, drive connection 16 of shaft 14 is received into drive socket 15 of lower shank 200. Washer 32 maybe provided between circumferential rim 204 of lower shank 200 and circumferential flange 30 extending radially inward within the hollow of cylindrical body 2. Washer 32 may be of a polymer or other material having low coefficient of friction. The cylindrical body is bisected into a front portion "A" and a back portion "B" by raised interior annular wall 33 forming a passageway fluidly connecting the front and back portions.

Figure 1A:
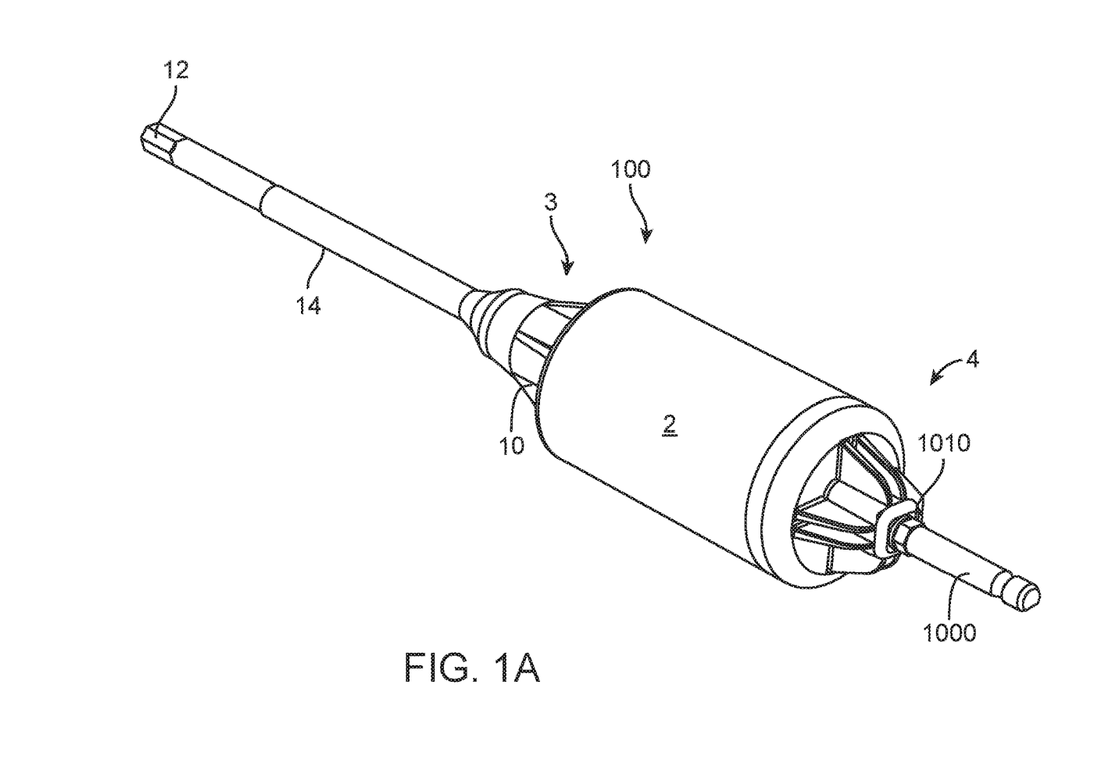
FIG. 1A shows a perspective back to front view of some aspects of a in line driver with modular clutch assembly.
Figure 1B:
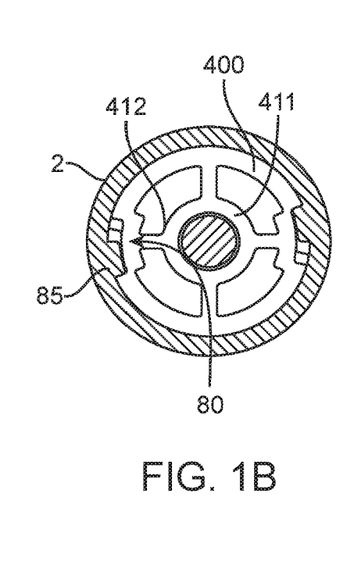
FIG. 1B shows a cutaway axial view of some aspects of a in line driver with modular clutch assembly.
Figure 2:
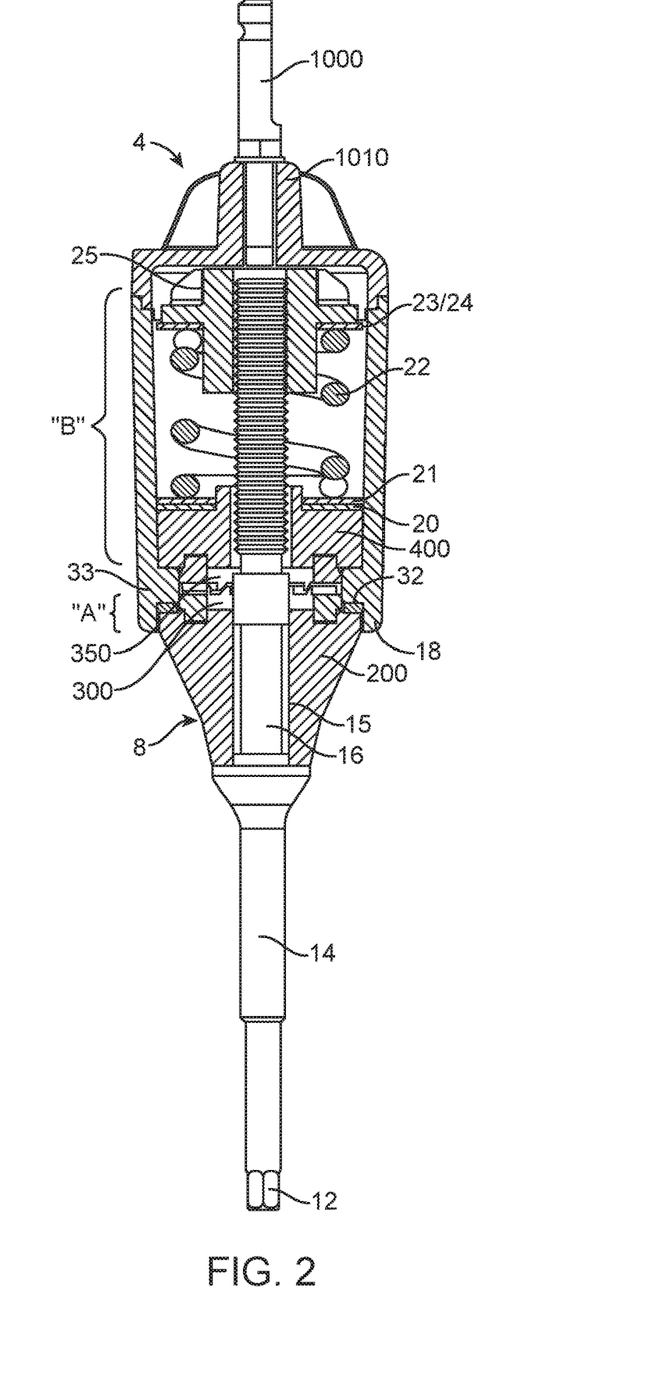
FIG. 2 shows a cutaway view of a driver with modular clutch assembly some aspects of a driver.

According to aspects of one or more exemplary implementations, integrally formed within cylindrical body 2, are one or more protrusions 85 which mate with recess 80 of upper shank 400. FIG. 1A and FIG. 3 illustrate protrusion 85. Protrusion 85 extends inward in a radial fashion and has a length along the axis of cylindrical body 2 for relative moveable engagement within recess 80. This engagement provides a locking mechanism of shaft 14 relative to the handle via upper shank 400 when pressure is applied across lower shank 200 and upper shank 400. Recess 80 is provided circumferentially wider than protrusion 85 for allowing cylindrical body 2 and the handle to rotate in reverse a predetermined distance from a locked position without subsequent reverse rotation of workpiece-engaging tip 12. Thus, at least one recess 80 and at least one protrusion 85 lock the handle in one direction providing the necessary torque to drive a fastener and allow for a predetermined amount of reverse rotation before unscrewing the fastener.

According to aspects of one or more exemplary implementations, force is applied across lower shank 200 with affixes first gear ring 300 and upper shank 300 with affixed second gear ring 350 via spring 22 within cylindrical body 2. Inside cylindrical body 2, shown in FIG. 2 washer 20 and washer 21 are provided between upper shank 400 and spring 22. Washer 20 and washer 21 transfer pressure from spring 22 over the top face of upper shank 400. At an end of spring 22 opposite upper shank 400, washer 23, washer 24 and nut 25 hold spring 22 in a relatively compressed state. Washers 23 and 24 are shown as one piece on FIG. 2 because in some instance they may be a single washer. Washer(s) provided between nut 25 and spring 22 facilitate relative rotation of nut 25 and spring 22. It has been shown in our testing that at higher forces above about 80 lbf-in that stainless steel washers 23 and 24 may allow too great a variation (over 10%) in torque applied in repeat cycles. Accordingly, ii is preferred at these forces that the washer 24 against the nut 25 is a Delrin washer. The results have shown that the torque is more stable and variations are reduced. Being a coil spring, the spring 22 has an internal pathway with a known diameter.

According to one or more exemplary implementations, shaft 14 having threading 17 at an end opposite workpiece-engaging tip 12 engages a complementary threading within nut 25, thereby imparting pressure between the respective first and second gear rings 300 and 350 of lower shank 200 and upper shank 400. Spring 22 and nut 25 provide the proper tensioning and biasing for the clutch. The clutch comprises an assembly including the upper shank 400, gear rings 300 and 350 and lower shank 200. The clutch is generally held together via the shaft 14 and nut 25 to provide proper tension and calibration.

According to aspects of one or more exemplary implementations, various materials may be used for the components of driver. According to some exemplary implementations, at least one of body 2, nut 25, lower shank 200, and upper shank 400 is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. According to aspects of one or more exemplary implementations, at least one of lower shank 200 and upper shank 400 is of or includes at least one material that lubricous or otherwise reduces friction thereby improving precision of the device.

According to aspects of one or more exemplary implementations, a single integrated shaft 14 spans the distance between workpiece-engaging tip 12 and an engagement point with nut 25. This configuration enables greater torque capabilities than a piecemeal or fragmented set of interconnected components. This reduces the number of interconnections between a source of a torque and a location to which the torque is transferred.

According to one or more exemplary implementations, shaft 14 having drive connection 16 between opposing extensions stabilizes drive connection 16 within drive socket 15. Placement of drive connection 16 at a medial segment of shaft 14-rather than at an end thereof-facilitates a more stable engagement between drive connection 16 and drive socket 9, thereby increasing the ability of engagement to transfer high amounts of torque.

According to one or more exemplary implementations, an engagement of drive connection 16 within drive socket 15 is maintained by the connection of the integrated portion of shaft 14 that extends to nut 25. According to some exemplary implementations, both threading 17 and drive connection 16 are of a single integrated structure (i.e., shaft 14). A force applied by spring 22 to nut 25 is directly transferred along shaft 14 from threading 17 to drive connection 16. This force securely maintains drive connection 16 within drive socket 15. This engagement enables transfers of greater amounts of torque from lower shank 200 (i.e., via drive socket 15) to shaft 14 (i.e., via drive connection 16).

According to aspects of some exemplary implementations, drive connection 16 and drive socket 15 have complementary geometries. One or more of a variety of configurations may be 15rovided for engaging drive connection 16 within drive socket 9. For example drives and associated connections may include triangular, square, hexagonal, rectangular, etc. According to aspects of one or more exemplary implementations, a substantially square drive connection 16 and drive socket 15 provide high torque transfer capabilities. Out of a variety of drive types, experiment15I results demonstrated that square drives and connections were among the most successful at transferring high torque without failure. Drive connection 16 and drive socket 15 may have rounded corners and edges to reduce or distribute stress risers.

According to aspects of one or more exemplary implementations, nut 25 may provide a lower portion or neck 26 having outer diameter substantially equal to an inner diameter of spring 22. The lower portion of nut 26 may extend axially through at least a portion of spring 22. The lower portion of nut 26 may maintain relative axial alignment between nut 25 and spring 22 by limiting travel of spring 22 other than by compression thereof.

According to aspects of one or more exemplary implementations, the disposable torque-limiting driver of the present disclosure is capable of imparting torques of up to about 120 inch-pounds. For example, the torque output range may be selected between about 60 inch-pounds and about 120 inch-pounds. Typically, the torque requirement is different for different operations and for different implants. For example, applications may include those in the field of orthopedic surgery, construction and emplacement of implants, etc. In such instances, the predetermined torque limit may be between about 60 inch-pounds and about 120 inch-pounds, depending on an implant's specifications.

In some instances, a torque-limiting driver, such as driver 100, may be prepackaged with an implant provided for one-time use. Such a methodology matches the driver that will impart a required amount of torque with the implant.

An exemplary implementation shows, at least in part, at cylindrical end 18, lower shank 200 provided, having an annularly tapering body and nose cone 8 along its length. Lower shank 200 may have a plurality of support flanges 10 that add strength while saving material. At one end, lower shank 200 tapers to drive shaft guide 15 at the end of the nose cone 8 molded to engage drive connection 16 of shaft 14. An exemplary implementation shows, at least in part, shaft 14 provided, at one end, with workpiece-engaging tip 12, adapted for engagement with an associated workpiece, such as a fastener or the like. Workpiece-engaging tip 12 is shown to be a geometrical connect but could be a socket wrench, screwdriver, wrench, or any other tool arrangement.

FIG. 3 shows aspects of the clutch assembly. Opposite the nose cone on the lower shank 200 are a plurality of lower dog cavities (LDC) 202 arranged in a face 203 with a circumferential rim 204 extending radially outward and an internal axial bore 205 to accommodate at least a portion of shaft 12 extending there through.

A first and second hardened gear ring 300 and 350 are interposed between the lower shank and upper shank 400 via reinforced catches wherein the hardened gear rings operate within a predetermined range of torque and duty cycles without failure. In some instances Hardened refers to a stainless steel gear ring. In other instances hardened refers to plastics or other metal or alloys such as Titanium and aluminum. One hardened material suitable for the gear ring is 440c stainless steel which will withstand at least 12 Newton-meters (Nm) of force over and 100 actuations. The hardened gears are functional over a number of cycles and force that would cause failure of a plastic gear arrangement such as that taught in International Application WO 2011/139902 which is hereby incorporated by this reference as if fully set forth herein. The predetermined range is preferably between 70 lbf-in and about 150 lbf-in, more preferably between about 90 lbf-in and about 135 lbf-in, most preferably between about 106 lbf-in and about 125 lbf-in. In some instance the torque range is above 125 lbf-in. In some instance the hardened gear must withstand at least 100 actuations and remain in a specified operational range. In some instance the hardened gear must withstand at least 50 actuations and remain in a specified operational range.

According to aspects of one or more exemplary implementations, inside cylindrical body 6 a clutch assembly is disposed. The clutch assembly includes first gear ring 300 and second gear ring one fixed to each of the shanks. In use the upper shank 300 and attached second gear ring 350 forcibly engages the first gear ring 300 and attached lower shank 200.

Upper shank 400 has a bottom face 402 and a front facing side 403, the front face 402 has a plurality of upper dog cavities (UDC) 405 and the upper shank 400 includes outer cylindrical shank 407 and axial bore 409 through inner shank 411. Inner shank 411 and outer shank 407 may be connected via inner supports arms 412, leaving upper shank 400 substantially hollow with internal spaces on a top face. Alternatively, upper shank 400 may be of a single contiguous piece. The upper shank also has recess 80 formed therein for engagement with a drive protrusion within the cylindrical body 2 (shown in FIG. 1B).

The four UDCs 405 are reinforced catches. The four LDCs 202 are also reinforced catches. Although four UDC and LDC are illustrated, the choice of four is not a limitation. Those of ordinary sill in the art will recognize that a fewer or greater number of UDC or LDC may be implemented depending on the material, use, force and duty cycle are within the scope of this disclosure. In some instance as few as two LDC or UDC in other instances three, four, five or even six LDC or UDC may be utilized. More than six LDC or UDCs would require a bottom face of enough area to provide separate cavities. The number of LDCs and UDS need not be equal. In some instances it is preferable to align one UDC with the recess 80. It is preferably to have at least 2 recesses on opposite sides of the outer shank 407. By aligning two of the UDCs with the recess 80 the load is distributed better across the shank. In some instances 2 or more arms 412 are opposite each other and one is aligned with the recess. The arm 412 placement above UDCs also provides additional support and strength.

FIG. 3 shows UDCs 405 as closed catches with an annular wall 415 and a substantially bottom 417. The bottom 417 secures the annular wall and provides additional strength to prevent failure. The bottom may be a completely closed region or it may have an open center region (not shown). The cavity structure of the LDC 202 is substantially the same as that of the UDC 405. The depth of the UDCs corresponds to the length of the preferably between about 0.069" and about 0.090" more preferably between about 0.069" and about 0.075" and most preferably about 0.072".

However, the depth and opening configuration of the UDC or LDC must be corresponding to the corresponding dogs that acted as catches therein. Specifically, the first gear ring 300 has an outer annular wall 302 and in inner annular wall 304 forming a ring with an open center 306 and dog latches 305 extending from a front side 307 and gears 310 extending from the backside 312 of the ring. Specifically, the second gear ring 350 has an outer annular wall 352 and in inner annular wall 354 forming a ring with an open center 356 and dog latches 355 extending from a front side 357 and gears 360 extending from the backside 362 of the ring. Length of a drive dog is preferable greater than the length of the opposing gear teeth so the lateral force generated by the gear teeth is less than the lateral force between the drive dog and the UDCs.

The length of each latch corresponds to the depth of each catch (UDC or LDC) however, it is small enough to fit into the cavity (catch). For purposes of a 0.072" catch depth for a UDC or LDC a suitable length for a dog latch would be about 0.062". The delta between depth and length is in part a factor of the UDC or LDC having a radiuses edge at its bottom connection with its annular wall and the dog latch should not extend so far as to damage the radiuses boundary. If the boundary radius was reduced the dog latch length could increase accordingly. For additional fortification, the length of dog latches are preferably longer than they are wide.

The width of the dog latches is relative to the anticipated force and the material. Since a steel dog will be interfacing with a softer material in the catch UDC or LDC, a dog latches' width should correspond to the anticipated force. The width and the thickness of the dogs create the surface area that apply the force to the catches. A greater width (more total surface area) applies less stress to the catch.

The gear ring should also sit flat against the face of the shank it is fit to. FIG. 3 shows the upper shank 400 with a bottom face 402 against which the front side 357 of the second gear ring will rest once the dog latches 355 are mated with the corresponding UDCs 405. The gear ring should seat completely against the mating surface of the bottom face 402 of the clutch prior to the gear ring drive dogs reaching the bottom of the cavities.

The thickness of the drive dog should be thicker than the thickness of the gear teeth 310/360 plus the gap between the opposing gear teeth when the device is static. This ratio of dog latch length to gear teeth presents a loose gear ring from becoming dislodged. Once assembled, there is typically about a 0.005" gap between the gear rings. The gap ensures the top of the teeth do not touch the base of the opposing gear ring. If the two features touch and drag against each other during actuations, that would affect the torque output and stability.

Those of ordinary skill in the art will recognize that in some instance that at least one of the hardened gear rings may be sonically bonded to a plastic shank, and that such sonic bonding is within the scope of this disclosure although it is less robust and its use will be dependent on the forces involved and the duty cycle required and such variation is within the scope of this disclosure. In some instances of less than the highest levels of torque sonic bonding may be added to add strength and allow for smaller UDC or LDC.

Those of ordinary skill in the art will recognize that in some instance that at least one of the hardened gear rings may , in addition to being fit into a face of a shank with dog latches in catches, may also be sonically bonded to the plastic shank and such variation is within the scope of this disclosure.

According to one or more exemplary implementations, upper shank 400 includes at least one recess 80 on a side of outer shank 407. Recess 80 is provided as a cylindrical cut, relief or recess into the side of the outer shank and maybe provided as a square or rectangular cut or the cut may have a slanted side or sides relative to the axis of upper shank 400, as shown in FIG. 3. According to aspects of one or more exemplary implementations, integrally formed within cylindrical body 2, protrusion 85 mates with recess 80 of upper shank 400 Protrusions 85 extends inward in a radial fashion and has a length along the axis of cylindrical body 2 for relative moveable engagement within recess 80. This engagement provides a locking mechanism of shaft 14 relative to the handle via upper shank 400 when pressure is applied across lower shank 200 and upper shank 400. Recess 80 is provided circumferentially wider than protrusion 85 for allowing cylindrical body 6 and the handle to rotate in reverse a predetermined distance from a locked position without subsequent reverse rotation of workpiece-engaging tip 12. Thus, at least one recess 80 and at least one protrusion 85 lock the handle in one direction providing the necessary torque to drive a fastener and allow for a predetermined amount of reverse rotation before unscrewing the fastener.

Figure 5A:
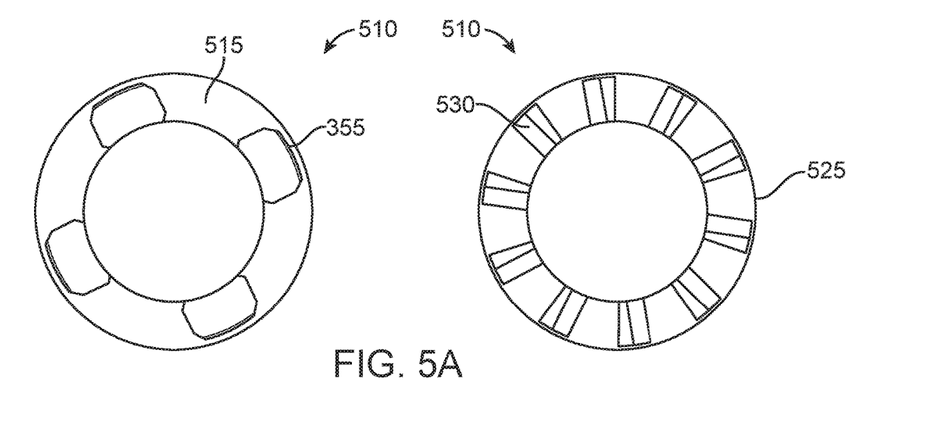
FIG. 5A shows a front and back view of a gear ring adapted to mate with a shank.
Figure 5B:
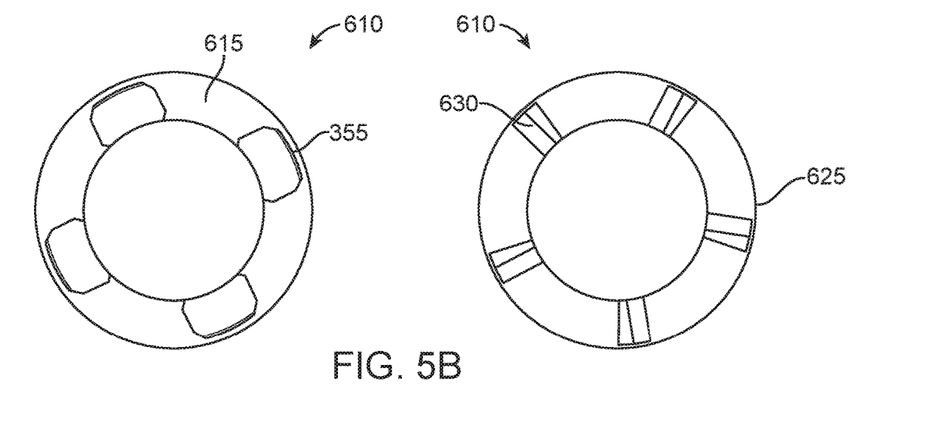
FIG. 5B shows a front and back view of a gear ring adapted to mate with the shank; and, FIG. 5C shows a front and back view of a gear ring adapted to mate with the shank.
Figure 5C:
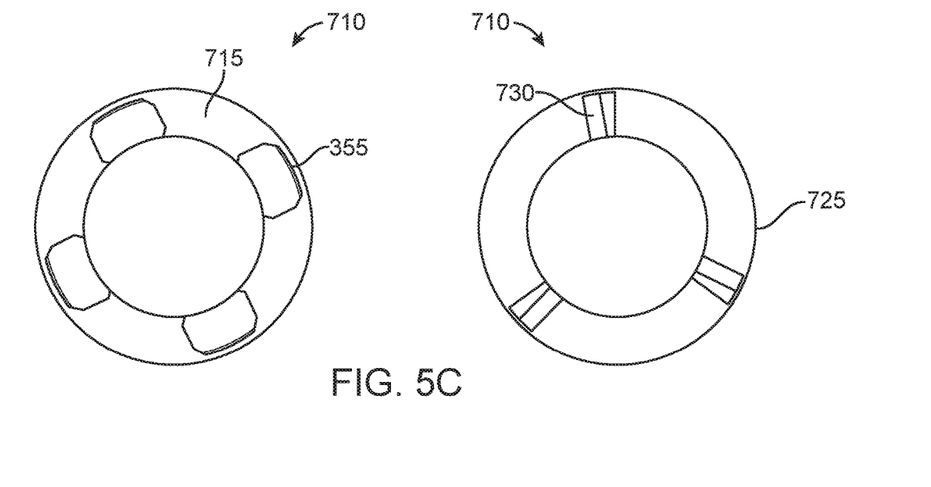

FIGS. 5A through 5C illustrate 3 variations on swappable gear rings for use in a torque limiting devices whereby a base set of shanks may support a variety of gear configurations. FIG. 5A the gear ring has a front side 515 which supports a dog latches 355 which correspond to the upper shank's UDCs 405. The gear ring has a back side 525 having gear teeth 530 extending therefrom in an in preselected configuration of nine teeth.

FIG. 5B the gear ring has a front side 615 which supports a dog latches 355 which correspond to UDCs 405. The gear ring has a back side 625 having gear teeth 630 extending therefrom in an in preselected configuration of five teeth.

FIG. 5C the gear ring has a front side 715 which supports a dog latches 355 which correspond to UDCs 405. The gear ring has a back side 725 having gear teeth 6730 extending therefrom in an in preselected configuration of three teeth.

Those of ordinary skill in the art will recognize that the above disclosure applies equally to the lower shank LDCs as opposed to the upper shank dog catches. And that the disclosure encompasses having swappable gear rings which may be used with one or both of the shanks.

In some instances, a torque-limiting driver, such as driver 100, may be prepackaged with an implant provided for one-time use. Such a methodology matches the driver that will impart a required amount of torque with the implant.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A clutch having swappable gear rings comprising:
   a lower shank (200) having lower dog catches (LDC) (202);
   the lower shank having an internal axial bore (205);
   a first gear ring (300) with gear teeth (310) extending from the backside (312) and a plurality of dog latches (305) extending from the front side (307);
   a upper shank (400) having upper dog catches (UDC) (405);
   the upper shank having an internal axial bore (409);
   a second gear ring (350) with gear teeth (360) extending from the backside (362) and a plurality of dog latches (355) extending from the front side (357);
   wherein the dog latches mates with the dog catches; and,
   the gear teeth on each of the first and second gear ring mate with each other.

2. The clutch of claim 1, wherein the gear rings are hardened.

3. The clutch of claim 2, wherein the hardened gear rings are 440c stainless steel.

4. The clutch of claim 3, wherein the gear teeth are one or more.

5. The clutch of claim 3, wherein the gear teeth are two or more.

6. The clutch of claim 3, wherein the gear teeth are three or more.

7. The clutch of claim 3, wherein the gear teeth are four or more.

8. The clutch of claim 3, wherein the gear teeth are five or more.

9. The clutch of claim 3, wherein the gear teeth are six or more.

10. The clutch of claim 3, wherein the gear teeth are seven or more.

11. The clutch of claim 3, wherein the gear teeth are eight or more.

12. The clutch of claim 3, wherein the gear teeth are nine or more.

13. The clutch of claim 3, further comprising a first washer between the spring, a second Delrin washer, and the nut.

14. A clutch having swappable gear rings comprising:
a lower shank (200) having lower dog catches (LDC) (202);
the lower shank having an internal axial bore (205);
a first gear ring (300) with gear teeth (310) extending from the backside (312) and a plurality of dog latches (305) extending from the front side (307);
a upper shank (400) having upper dog catches (UDC) (405);
the upper shank having an internal axial bore (409);
a second gear ring (350) with gear teeth (360) extending from the backside (362) and a plurality of dog latches (355) extending from the front side (357);
wherein the dog latches are longer than the gear teeth;
wherein the dog latches mates with the dog catches; and,
the gear teeth on each of the first and second gear ring mate with each other.

15. A torque-limiting driver with swappable clutch gear rings comprising:
a body (2) which may act as a handle;
a lower cylindrical shank with a first hardened gear ring affixed via dog latches and catches to the face thereof having a drive socket (15) through the nose (8) at the opposite side;
an upper cylindrical shank with a second hardened gear ring affixed via dog latches and catches to the bottom face (402) and having a front facing side (403);
a nut (25);
a spring (22) between the front facing end the upper cylindrical shank and the nut,
wherein the spring is configured to apply a force across the gear rings;
a shaft (14) having a workpiece-engaging tip (12) and a drive connection (16) engaged within the drive socket of the lower cylindrical shank, the shaft extending axially through the lower cylindrical shank, the hardened first gear ring, the second hardened gear ring, the upper cylindrical shank and the spring and connected to the nut;
wherein the hardened gear ring of the upper cylindrical shank and the hardened gear ring of the lower cylindrical shank engage for relative rotation; and,
wherein the gear rings disengage when a predetermined torque limit is exceeded.

16. The driver of claim 15, wherein the shaft includes a threading (17) that is threaded onto the nut.

17. The torque-limiting driver of claim 16, wherein a force provided by the spring securely maintains the drive connection of the shaft engaged within the drive socket of the lower cylindrical shank.

18. The torque-limiting driver of claim 17, further comprising at least two washers (21/20) between the spring and the upper cylindrical shank.

19. The torque-limiting driver of claim 17, further comprising a washer (32) between the lower cylindrical shank and the body.

20. The driver of claim 17 wherein the engaged gear rings and affixed shanks will provide a predetermined torque of at least 12 Newton-meters (Nm) of force over at least 100 actuations.

21. The driver of claim 17 wherein the predetermined torque limit is between about 110 inch-pounds and about 130 inch-pounds.

22. The driver of claim 15 wherein the engaged gear rings and affixed shanks will provide a predetermined torque of at least 12 Newton-meters (Nm) of force over at least 20 actuations.

23. The driver of claim 15 wherein the engaged gear rings and affixed shanks will provide a predetermined torque of at least 12 Newton-meters (Nm) of force over at least 50 actuations.

* * * * *